US009363098B2

(12) United States Patent
Hamida et al.

(10) Patent No.: US 9,363,098 B2
(45) Date of Patent: Jun. 7, 2016

(54) METHOD OF EVALUATING THE QUALITY OF RADIO LINKS FOR A WIRELESS BODY AREA NETWORK, METHOD OF TRANSMITTING MESSAGES FOR A WIRELESS BODY AREA NETWORK, AND DEVICES FOR IMPLEMENTING THOSE METHODS

(75) Inventors: Elyes Ben Hamida, Grenoble (FR); Denis Benoit, Grenoble (FR)

(73) Assignee: Commissariat a l'energie atomique et aux energies alternatives, Paris (FR)

(*) Notice: Subject to any disclaimer, the term of this patent is extended or adjusted under 35 U.S.C. 154(b) by 315 days.

(21) Appl. No.: 13/419,095

(22) Filed: Mar. 13, 2012

(65) Prior Publication Data

US 2012/0250546 A1 Oct. 4, 2012

(30) Foreign Application Priority Data

Apr. 1, 2011 (FR) ...................................... 11 52843

(51) Int. Cl.
*H04W 24/00* (2009.01)
*H04L 12/26* (2006.01)
*H04W 72/08* (2009.01)
(Continued)

(52) U.S. Cl.
CPC .......... *H04L 12/2602* (2013.01); *A61B 5/0028* (2013.01); *H04L 43/00* (2013.01); *H04W 72/085* (2013.01); *A61B 5/0006* (2013.01); *A61B 5/0008* (2013.01); *H04L 43/08* (2013.01);
(Continued)

(58) Field of Classification Search
CPC .......... H04M 2250/02; H04M 1/6066; H04M 1/7253; G06F 19/3468; G06F 19/3406; G06F 19/3481

USPC .................................................. 370/225–228
See application file for complete search history.

(56) References Cited

U.S. PATENT DOCUMENTS

2002/0062388 A1* 5/2002 Ogier et al. ................... 709/238
2002/0085503 A1* 7/2002 Hulyalkar et al. ............ 370/252
(Continued)

FOREIGN PATENT DOCUMENTS

WO WO 2010/001320 1/2010
WO WO 2010/018517 2/2010
WO WO 2010/073180 7/2010

OTHER PUBLICATIONS

IEEE Standard 802.15.4-2006, "Wireless MAC and PHY Specification for Low-Rate WPANs", IEEE Computer Society, Sep. 2006.*
(Continued)

*Primary Examiner* — Khaled Kassim
*Assistant Examiner* — Zhaohui Yang
(74) *Attorney, Agent, or Firm* — Occhiuti & Rohlicek LLP

(57) ABSTRACT

A method for evaluating quality of radio links for a wireless body area network includes first and second wireless devices forming a body area network and configured to communicate with each other. One of the two wireless devices is mobile relative to the other, The method includes exploiting messages received by one of the wireless devices to measure instantaneous quality of a corresponding radio link and to estimate times during and between which a radio link is reliable, calculating an estimated times reliability indicator, and classifying the radio links as a function of the reliability indicator into at least first and second categories. One of these categories is a category relating to intermittently reliable radio links taking into account the mobility of the wireless devices of the body area network.

20 Claims, 11 Drawing Sheets

(51) Int. Cl.
*H04W 84/18* (2009.01)
*A61B 5/00* (2006.01)

(52) U.S. Cl.
CPC ........ *H04L 43/0852* (2013.01); *H04L 43/0894* (2013.01); *H04W 84/18* (2013.01)

(56) References Cited

U.S. PATENT DOCUMENTS

| | | | |
|---|---|---|---|
| 2006/0098608 A1* | 5/2006 | Joshi | 370/338 |
| 2007/0109972 A1* | 5/2007 | MacDonald | 370/252 |
| 2007/0133556 A1* | 6/2007 | Ding et al. | 370/395.4 |
| 2007/0253021 A1* | 11/2007 | Mehta et al. | 358/1.15 |
| 2008/0013458 A1 | 1/2008 | Kim | |
| 2008/0232375 A1* | 9/2008 | Hachiya et al. | 370/392 |
| 2011/0085442 A1* | 4/2011 | Lin et al. | 370/235 |
| 2011/0137133 A1* | 6/2011 | Espina Perez | 600/300 |
| 2011/0269414 A1* | 11/2011 | Falck et al. | 455/100 |
| 2012/0106397 A1* | 5/2012 | Abedi | 370/255 |

OTHER PUBLICATIONS

Becher, Alexander et al., "*Towards Short-Term Wireless Link Quality Estimation.*" In Hot Emnets, 2008.

Reusens, Elisabeth et al., "*Characterization of On-Body Communication Channel and Energy Efficient Topology Design for Wireless Body Area Networks.*" IEEE Transactions on Information Technology in Biomedicine, vol. 13, No. 6, Nov. 2009, pp. 933-945.

C. Gomez, "Problem Statement and Requirements for 6LoWPAN Routing draft-ietf-6lowpan-routing-requirements-05," IETF Trust, Feb. 21, 2010.

* cited by examiner

METHOD OF EVALUATING THE QUALITY OF RADIO LINKS FOR A WIRELESS BODY AREA NETWORK, METHOD OF TRANSMITTING MESSAGES FOR A WIRELESS BODY AREA NETWORK, AND DEVICES FOR IMPLEMENTING THOSE METHODS

RELATED APPLICATIONS

Under 35 USC 119, this application claims the benefit of the priority date of French Patent Application 1152843, filed Apr. 1, 2011, the contents of which are herein incorporated by reference.

TECHNICAL FIELD

The present invention concerns a method of evaluating the quality of radio links for a wireless body area network, a method of transmitting messages for a wireless body area network, and devices for implementing those methods.

The present invention concerns any application necessitating an exchange of data between wireless devices worn on the scale of a body at least some parts of which are mobile, for example a human being, but also a machine in motion.

At present it appears inevitable that in the medium term there will appear intelligent, autonomous wireless body area networks capable of addressing the requirements of emerging applications in fields as varied as security, health, sport and mass entertainment.

In this context, an important strategic stake is the development of more robust communication protocols adapted to the inherent properties and constraints of these wireless body area networks, essentially linked to mobility and to highly specific phenomena of propagation around the human body (e.g. obstruction or masking of radio links, etc.).

There may be cited by way of example applications using communication between the various wireless devices forming the body area network:
- Applications of navigation and of positioning groups of mobile persons in interior environments and global positioning services.
- Movement capture, for example for tracking sporting gestures or for entertainment and games applications.
- Posture detection, for example for rehabilitation, monitoring of vulnerable or aged persons, and surveillance of persons moving around in a hazardous environment (e.g. fire-fighters inside a burning building, etc.).
- Medical applications such as pacemakers, insulin pumps, surveillance/monitoring of vital signs (temperature, heartbeat [ECG—electrocardiogram], etc.).
- "Exploded terminal" type applications (screens, keyboards, earphones that are not co-located).

PRIOR ART

With recent technological advances in the fields of integration and miniaturization, and thanks to the development of low bit rate and very low consumption wireless communication technologies, e.g. Bluetooth™ Low Energy (BLE), Zigbee™ and IR-UWB (Impulse Radio Ultra WideBand), a new application field has emerged under the name of wireless body area networks (BAN).

For example, there is known from the document WO 2010/018517 a body area network that is designed to create a network of sensors worn by a patient, for example, or implanted in the patient to monitor certain vital parameters of the patient.

In this type of application, wireless devices form a network on or very near the human body: emblematic application examples may be cited such as the "exploded terminal" (screens, keyboards, earphones that are not co-located), sports equipment (heart rate meter, watch, pedometer on the shoe) or medical equipment (mobile cardiac, cerebral, muscular monitoring).

A body area network (BAN) is generally constituted by a set of wireless devices constrained in terms of energy, computation and storage capacity, attached to (or implanted in) the human body to form a self-organized and autonomous network. Each wireless device is able to collect local information by means of onboard sensors (positions, temperature, ECG, etc.) and to communicate with the other devices with a view to routing the collected data to a central device, also called a coordinator. The principal role of this coordinator is to serve as a gateway between the body area network and an exterior network (for example the Internet, a cellular network, another network of sensors, etc.).

FIG. 1 shows an example of a wireless body area network for the medical surveillance of a patient. In this figure, a patient or user U wears various wireless devices 3 equipped with one or more sensors, for example to monitor an implant or the blood pressure, heartbeat, vision, strength of the patient, the level of sugar in the blood, etc.

These wireless devices 3 are connected via a radio link to a central node 5 (generally adopting the role of the wireless network coordinator) that is configured to communicate with an external network 6, for example via an access point to a WLAN 7, a cellular telephone 9, etc. To this network are also connected, for example, emergency medical services or surveillance services 11, for example to alert an ambulance in the event of detection of an anomaly by one of the sensors.

Given the inherent characteristics of body area networks, some current communication techniques and protocols, notably those proposed in the context of wireless sensor networks (WSN) or wireless personal area networks (WPAN) are not suitable.

Wireless body area networks introduce numerous new constraints, linked essentially to the limited capacities of the wireless devices, the nature of the propagation channel, the mobility of the human body, and the particular topology of the network, necessitating new and more suitable communication strategies.

This can be illustrated in more detail by a very simple example. Consider that each of the wireless devices 3 is a node of a body area network BAN, that its functioning produces its own information to be transmitted over that network, and that it may also serve as a relay for other sensors of the network for routing data.

To save energy and thus to increase the autonomy of the network, it may be preferable, for example, to transmit data coming from a pedometer fixed to the heel via a wireless device serving as a relay installed at the level of the hip to the coordinator central node 5 instead of transmitting that data directly to the central node 5 without relaying it. In this context, account must also be taken of the fact that the transmission power is low, to respond to the IEEE 802 standards fixing permissible transmission powers for personal area network.

The mobility of the entity wearing or carrying these wireless devices (e.g. the patient, the human being) nevertheless imposes other restrictions.

Consider on the one hand a sensor worn at the level of the wrist of a human being and that the human being concerned is walking briskly, the arm swinging as they move and regularly finding itself level with or in their back. As a result, if the central node 5 (or coordinator) is at the level of the chest at the front, the data may not be transmitted directly to this central node 5, given that when the arm is in the rear position no radio link can be established sufficiently reliably with the central node 5 because of masking of the radio waves and/or the low transmission power of the wireless devices.

To alleviate these problems, it is therefore preferable to provide a wireless node or device serving as a relay that can always establish a reliable link on the one hand with the wireless device worn on the wrist and on the other hand either with another wireless device or directly with the central node 5.

A paper by A. Becher et Al. "Towards Short-Term Wireless Link Quality Estimation. In Hot Emnets, 2008" concerns wireless sensor networks and introduces the concept of a link that is reliable in the short term and potential use thereof in routing data.

Although the above paper concerns low-power radio links and suggests the use of radio links having short-term reliability, it does not take account of the specific nature of the body area networks and in particular of the mobility between a transmitter and a receiver.

The present invention aims to alleviate the aforementioned drawback, at least in part by proposing a method of evaluating the quality of radio links for a body area network already enabling identification and qualification of another category of potentially interesting links for routing and relaying information (packets) across the body area network and thereafter at all times improved exploitation of all the available radio links of the body area network.

To be more precise, the present invention aims to improve the performance of body area networks at least partially and as a function of the application context, for example in terms of connectivity, energy consumption, latency, reliability, data delivery rate, communication reliability, robustness of protocols to face dynamic variation of propagation conditions and/or the mobility of the human body.

To this end, the invention proposes a method of evaluation of the quality of the radio links for a wireless body area network comprising at least first and second wireless devices forming a body area network and liable to communicate with each other, at least one of the two wireless devices is liable to be mobile relative to the other, in which method:

messages received by at least one of the wireless devices are exploited and the instantaneous quality of the corresponding radio links is measured and the times during and between which a radio link is reliable are estimated, which method is characterized in that
an estimated times reliability indicator is calculated, and the radio links are classified as a function of the reliability indicator into at least two categories including a category relating to the intermittently reliable radio links taking into account the mobility of the wireless devices of the body area network.

Thus there is introduced a new category of links relating to the intermittently reliable radio links that takes account of the mobility of the wireless devices relative to each other.

Thanks to the invention, it is thus possible to determine the presence of links that will be reliable in the short term (or links for which the reliability is intermittent) and estimate the main characteristics, notably the contact time (time during which a radio link may be established and is reliable) and the intercontact time (the necessary time before the link is re-established after a break in connectivity).

This then enables prediction of the appearance/disappearance of these radio links, and the respective contact/intercontact times, with a view to improving the performance of the communication protocols (for example the routing and relaying of packets, scheduling of communications, etc.), in terms of energy consumption, latency, data delivery rates, etc.

Returning to the example of the wireless device fixed to the wrist, a direct radio link between that wireless device and the central node may be established intermittently, enabling further reduction of the radio transmission power and thus in the end of the energy consumption of the body area network.

According to one or more features of the method, taken separately or in combination:

the messages exchanged between the wireless devices are service messages, data messages or a combination of those messages, these messages are exchanged periodically or pseudoperiodically, these messages are exchanged at a variable frequency, the instantaneous quality of the radio links is evaluated by measuring at least one radio indicator such as RSSI, LQI or SNR, the instantaneous quality of the radio links is evaluated by measuring a connectivity parameter, the connectivity parameter and/or the radio indicator is/are determined in binary fashion having a value "1" or a value "0" $L_{i,j}^{[t]} = \{0,1\}$ for any time t, between a node i and j, i≠j, for example:

$$L_{i,j}^{[t]} = \begin{cases} 1 & \text{if the link is active, for example if a message has succeeded} \\ 0 & \text{if the link is inactive, for example if a message has failed} \end{cases}$$

alternatively:

$$L_{i,j}^{[t]} = \begin{cases} 1 & \text{if the radio indicator is greater than or equal to a threshold} \\ 0 & \text{if the radio indicator is less than a threshold} \end{cases}$$

to classify the radio links according to at least two categories, there is determined from the connectivity parameter or from the radio indicator for two respective wireless devices contact and intercontact times and the presence of repetitive patterns of intermittent contact is determined, the contact time $\hat{C}_{i,j}^{[t]}$ is calculated as being the duration of a binary sequence $L_{N+M} = \{L_{i,j}^{[1]}, L_{i,j}^{[2]}, \ldots, L_{i,j}^{[N+M]}\} \in \{1\}^N$ and $\{0\}^M$ and such that $$\frac{N-M}{N} \geq \gamma_F,$$

where $\gamma_F$ is a reliability threshold of the radio link, the intercontact time $\hat{I}_{i,j}^{[t]}$ is calculated as being the duration of a binary sequence $L_{N+M} = \{L_{i,j}^{[1]}, L_{i,j}^{[2]}, \ldots, L_{i,j}^{[N+M]}\} \in \{1\}^N$ and $\{0\}^M$ and such that $N \leq \gamma_{UP}$, where $\gamma_{UP}$ is the maximum number of "1" tolerated during the intercontact period, the final contact and intercontact times are calculated from the following formulae:

$$C_{i,j}^{[t]}(\alpha_{CT}) = \alpha_{CT} \times C_{i,j}^{[t-1]} + (1 - \alpha_{CT}) \times \hat{C}_{i,j}^{[t]}$$

$$I_{i,j}^{[t]}(\alpha_{CT}) = \alpha_{CT} \times I_{i,j}^{[t-1]} + (1 - \alpha_{CT}) \times \hat{I}_{i,j}^{[t]}$$

where
$\hat{C}_{i,j}^{[t]}$, respectively $\hat{I}_{i,j}^{[t]}$, is the instantaneous estimate of the contact, respectively intercontact, time;

$C_{i,j}^{[t]}$, respectively $I_{i,j}^{[t]}$, is the final estimate at the time t of the contact, respectively intercontact, time; and $\alpha_{CT}$ is a forget factor, a moving coefficient of variation $V_{i,j}^{[t]}$ is calculated over a window of size $W_V$ that is defined as being the ratio between the standard deviation and the mean of the estimates over a moving window of size $W_V$ and it is compared to a threshold $\gamma_V$ so that if the moving coefficient of variation $V_{i,j}^{[t]}$ is below the threshold $\gamma_V$ a link is classified as intermittently reliable and if it is greater than or equal to the threshold; if not it is classified as not being reliable, for each wireless device the reliability of the radio links is stored in a table of neighbours.

The invention also concerns a device for evaluating the quality of the radio links for a wireless body area network comprising a plurality of wireless devices comprising at least first and second wireless devices forming a body area network and liable to communicate with each other, at least one of the two wireless devices is liable to be mobile relative to the other, for implementing a method as defined hereinabove, characterized in that it comprises means configured to:

exploit messages received by at least one of the wireless devices and measure the instantaneous quality of the corresponding radio links, estimate times during and between which a radio link is reliable, calculate a reliability indicator for the estimated times, and classify the radio links as a function of the reliability indicator into at least two categories including a category relating to the intermittently reliable radio links taking into account the mobility of the wireless devices of the body area network.

The invention further concerns a method of transmitting messages across a wireless body area network characterized in that the quality of the radio links for a wireless body area network is evaluated by a method as defined hereinabove for routing or relaying and in that for the transmission of messages the messages are routed via an intermittently reliable radio link.

This method may further comprise one or more of the following features separately or in combination:

the messages are routed during a period for which the intermittently reliable radio link is considered reliable, the transmission of a message is favoured via an intermittently reliable radio link to optimize at least one of the parameters of the following group: energy consumption, latency, data delivery rate, the measurements of the distances between the wireless devices are scheduled taking account of the predicted appearance and/or disappearance of the intermittently reliable links.

The invention further provides a device for transmitting messages across a wireless body area network for implementing a message transmission method as defined hereinabove characterized in that it comprises means configured to evaluate the quality of the radio links for a wireless body area network for routing exchange of data and/or relaying of packets between the wireless devices using a method of evaluating the quality of the radio links for a wireless body area network as defined hereinabove and means configured to route the messages via an intermittently reliable radio link during a period during which the intermittently reliable radio link is considered reliable.

Other advantages and features will become apparent on reading the description of the invention and examining the following figures, in which.

Figure 3:
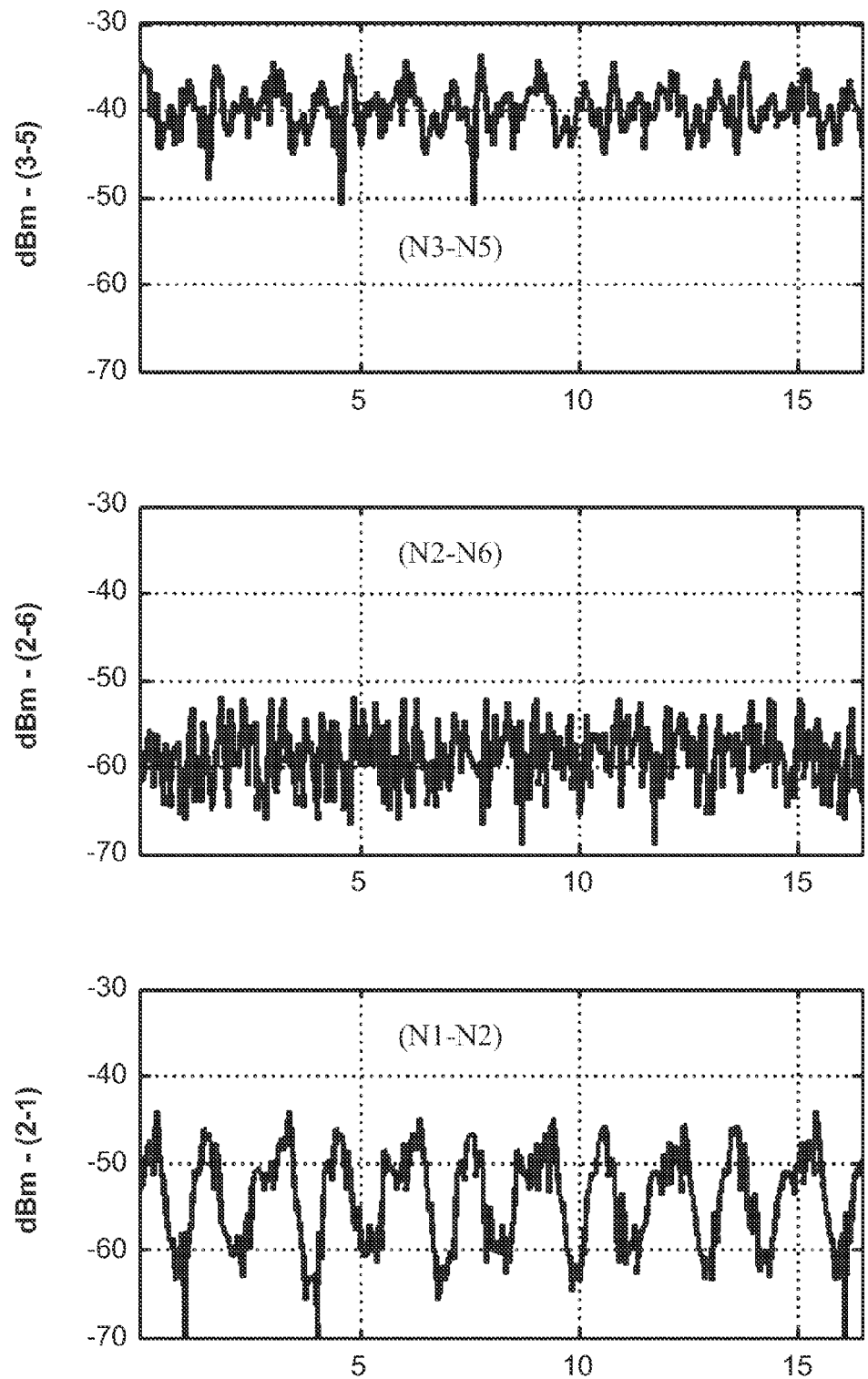
Figure 4:
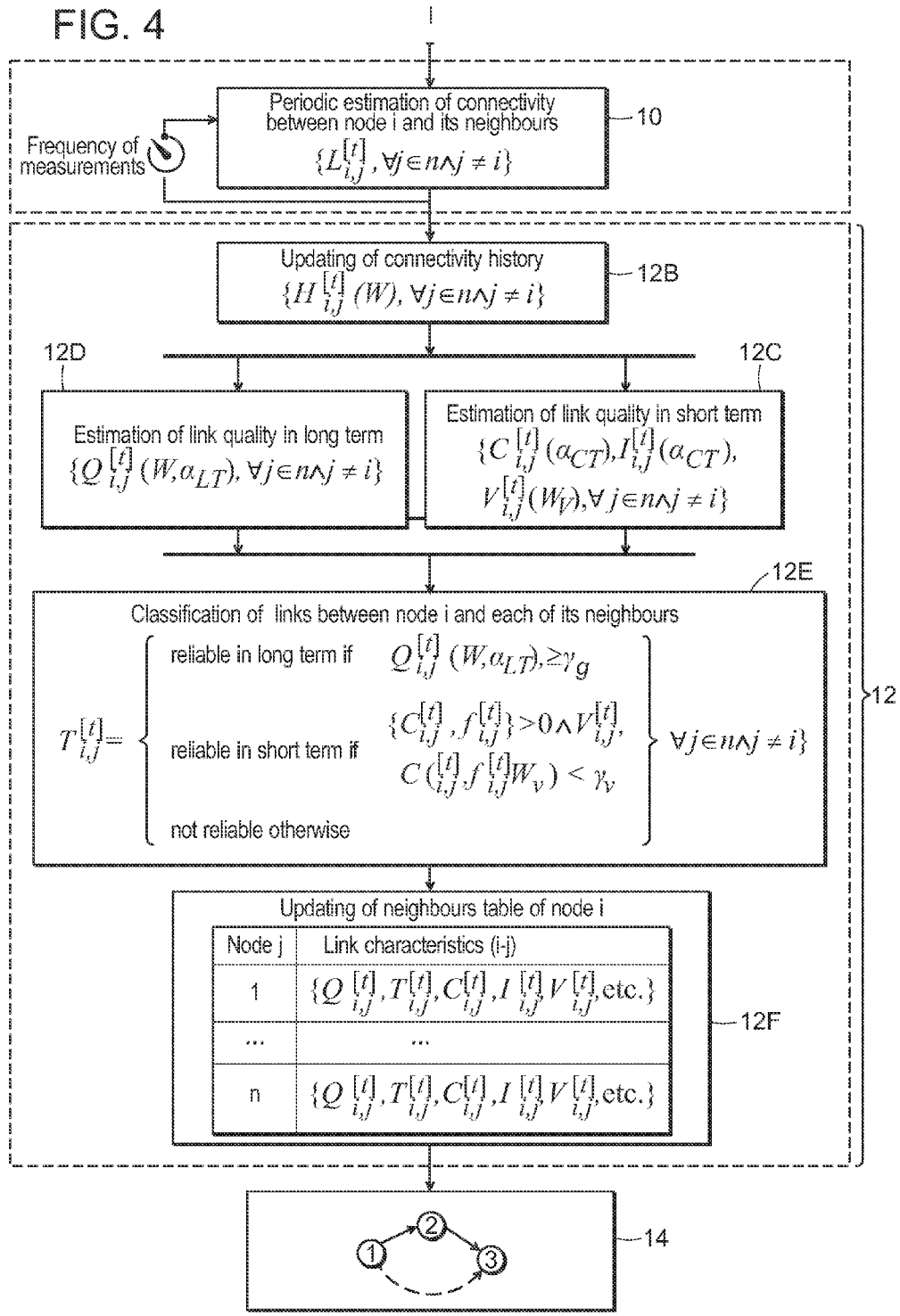
Figure 5:
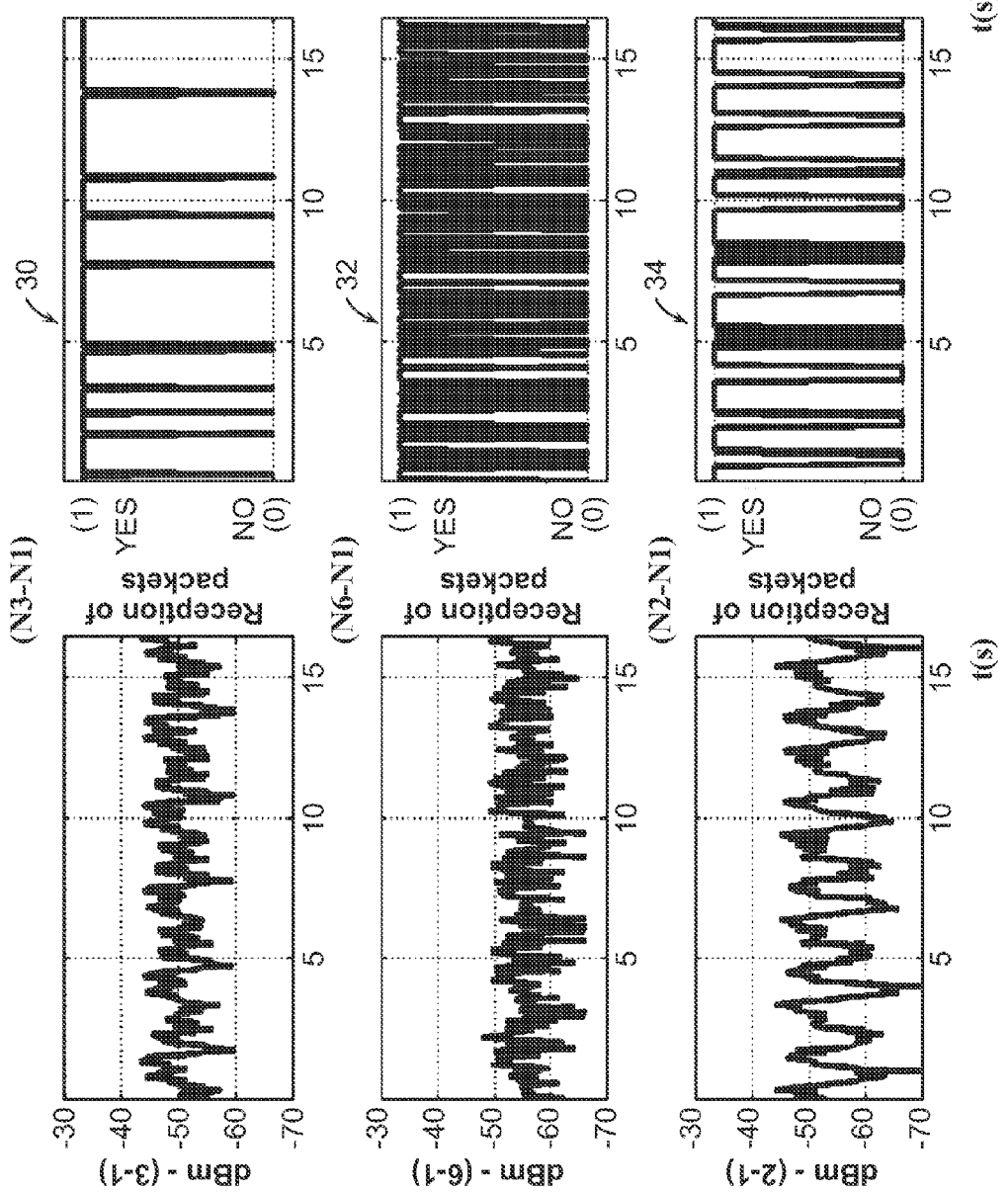
Figure 6:
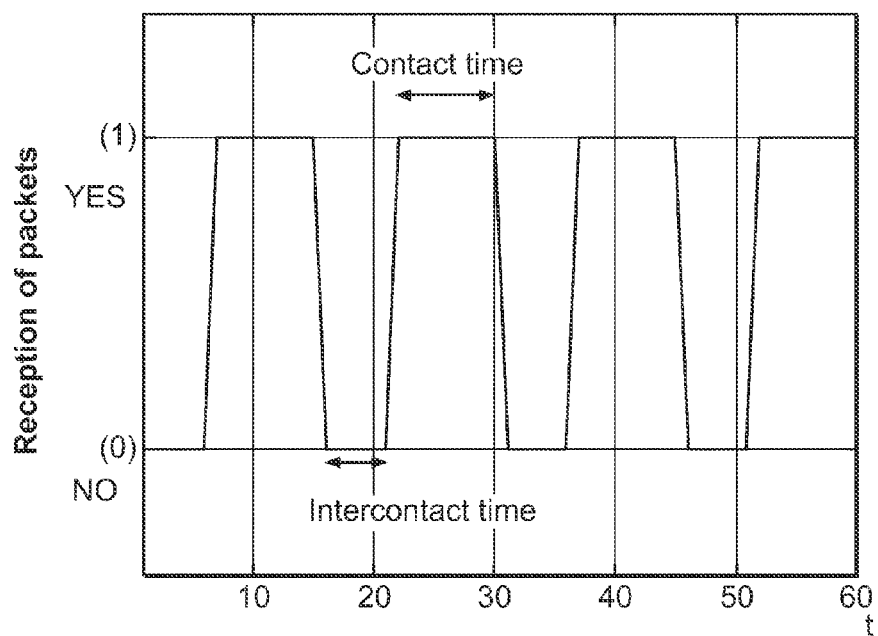
Figure 7:
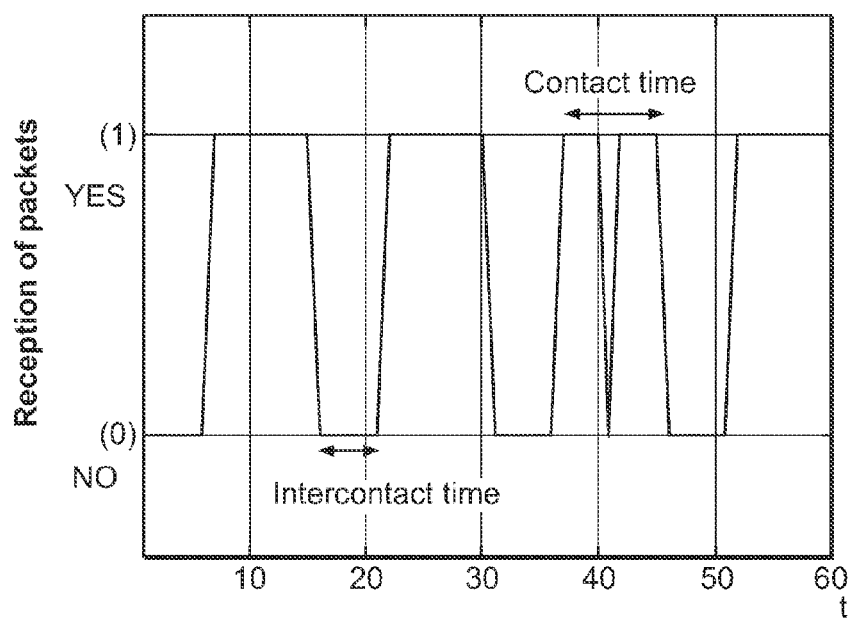
Figure 8:
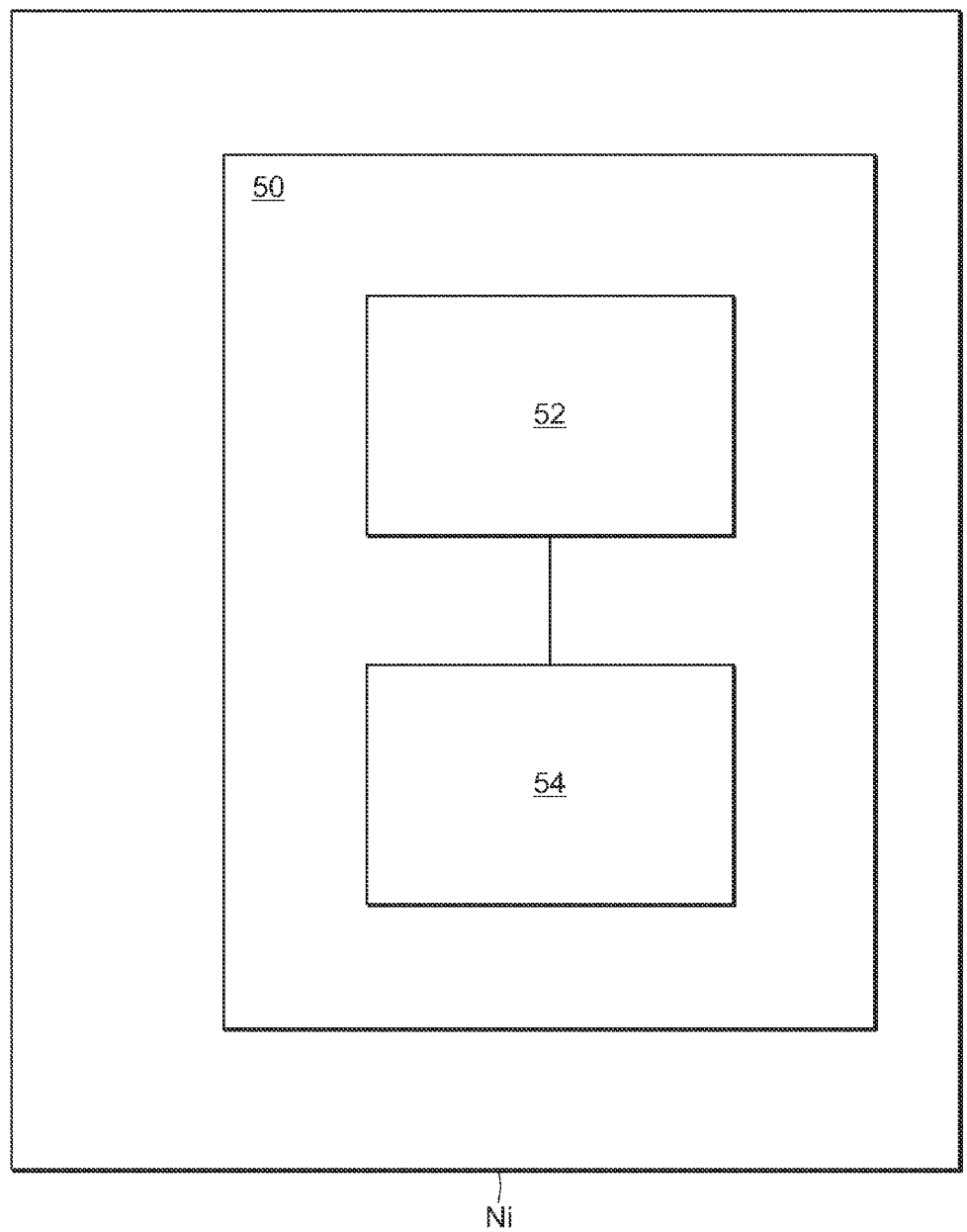
Figure 9:
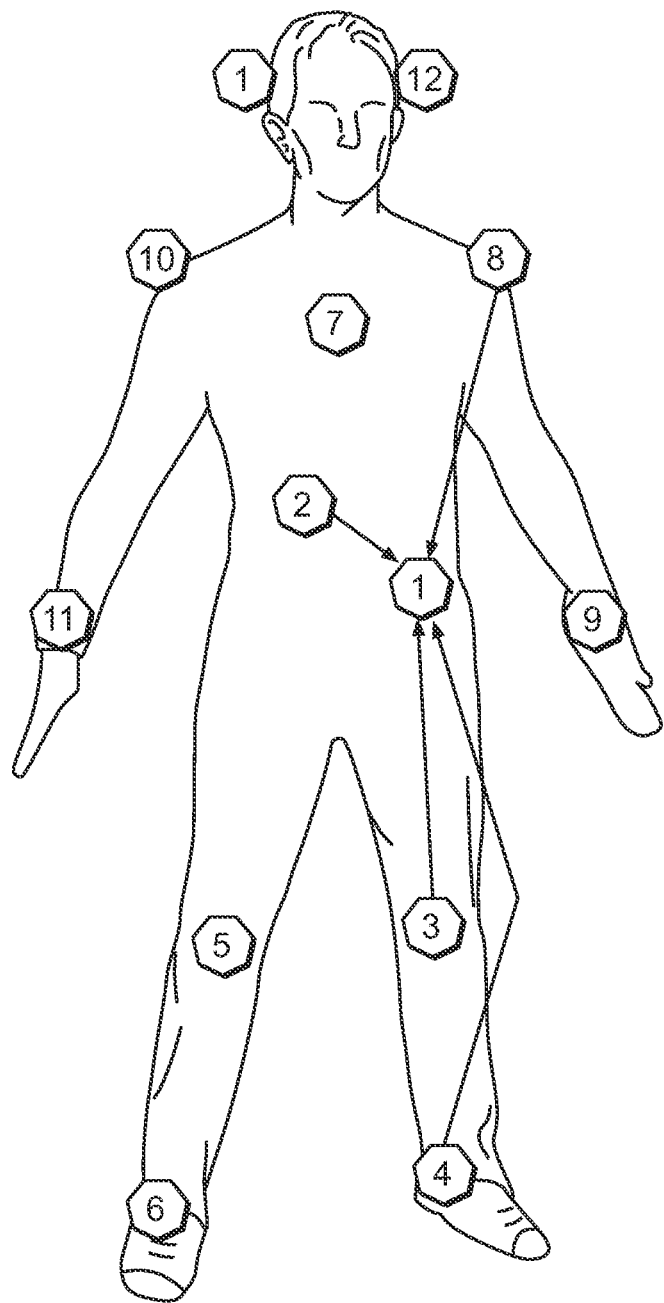
Figure 10:
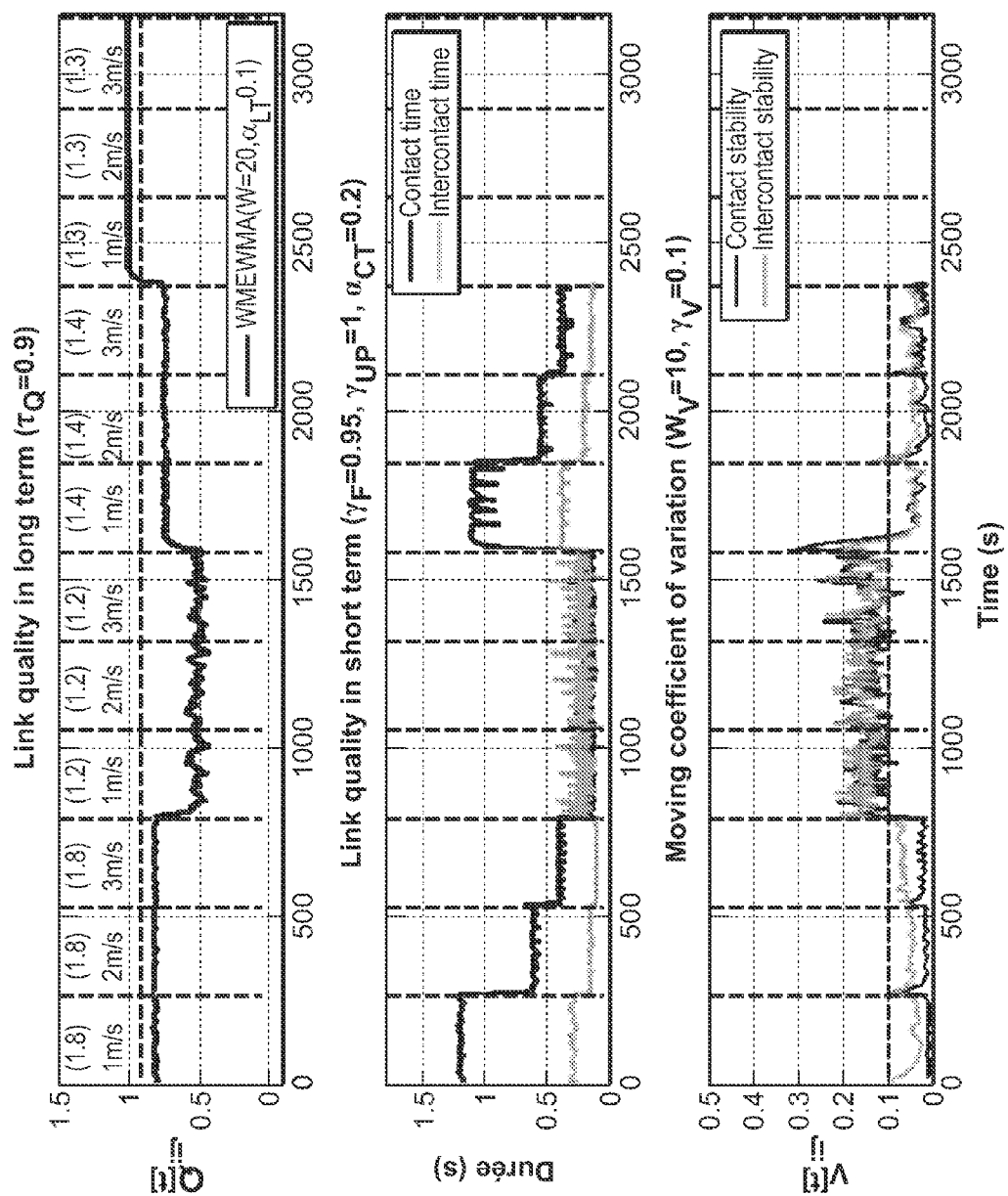
Figure 11:
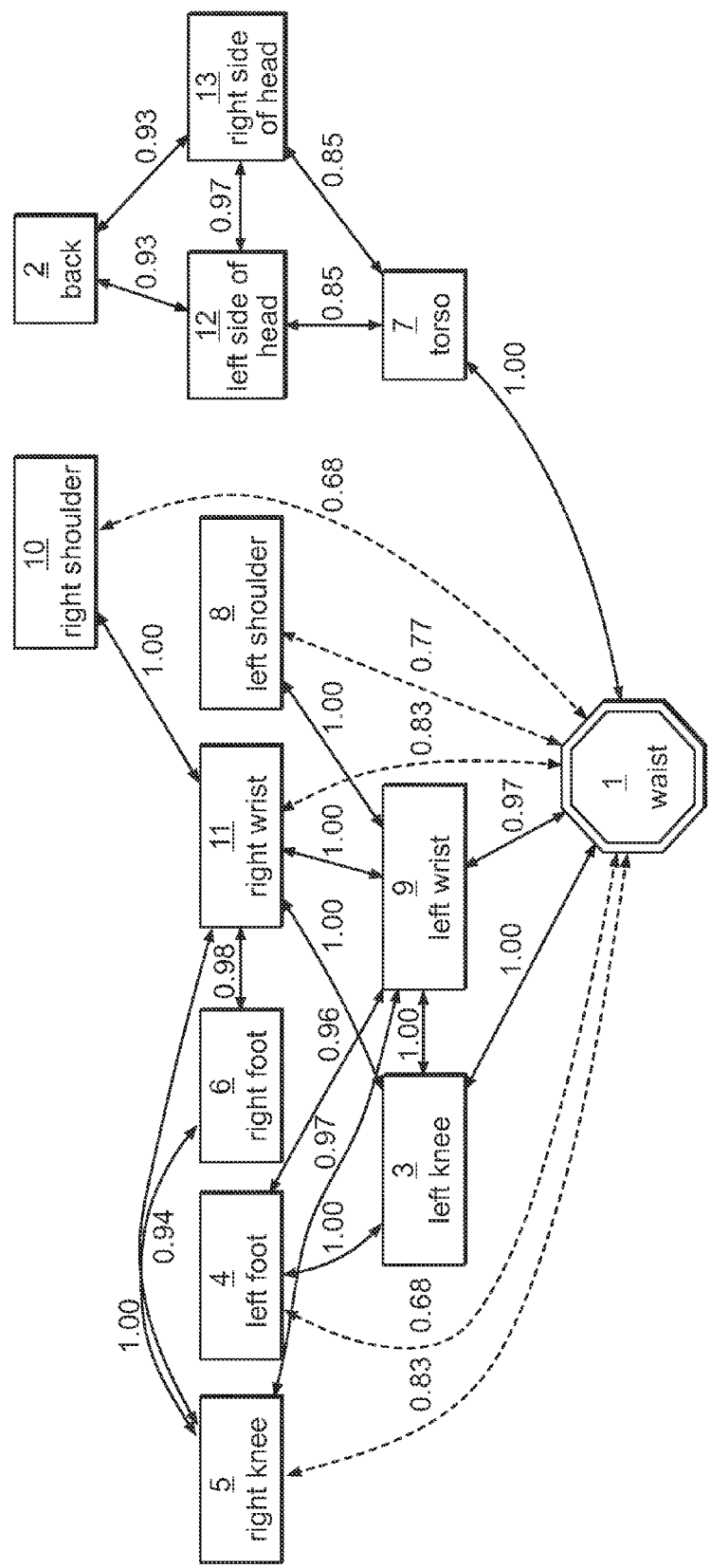
Figure 12:
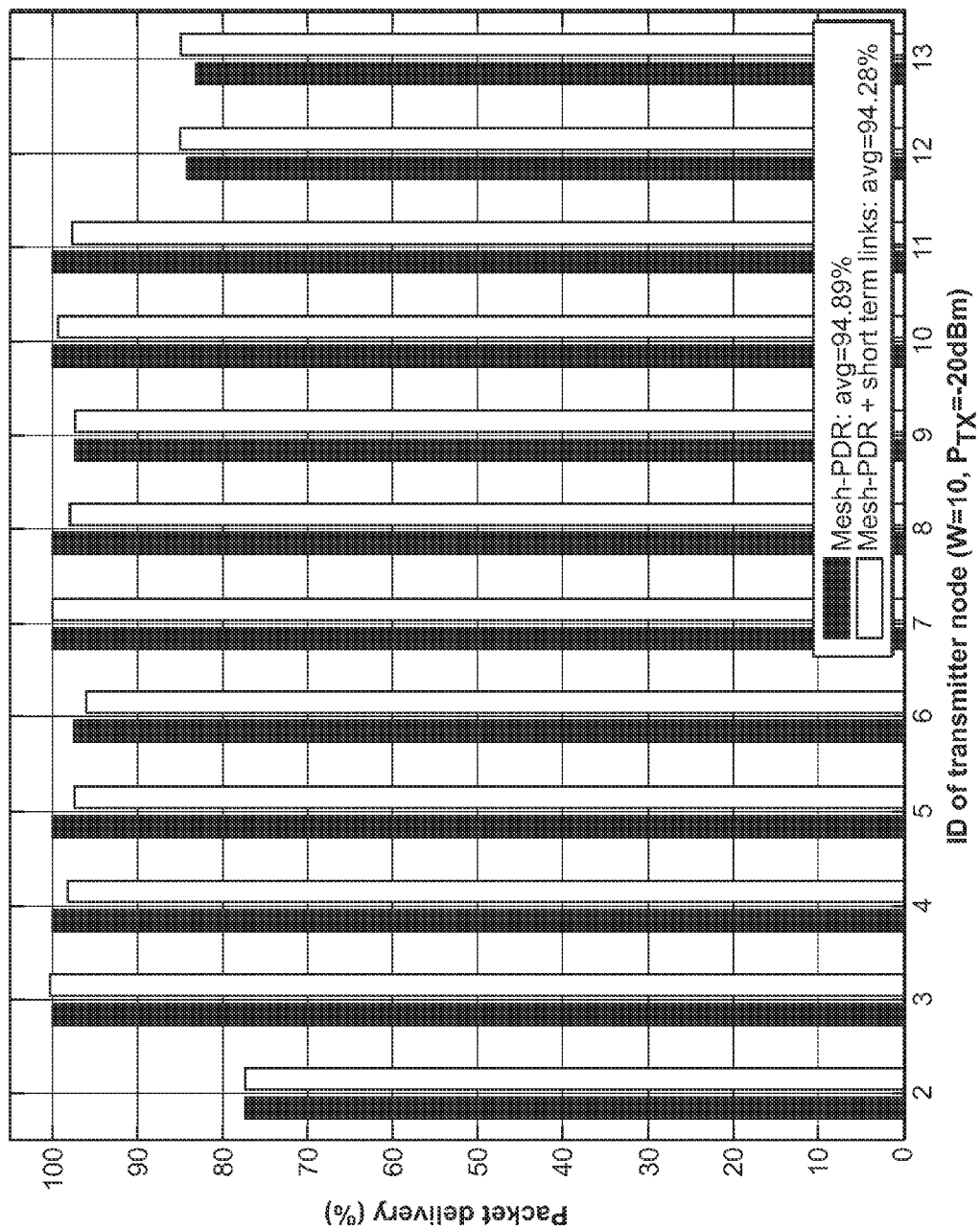
Figure 13:
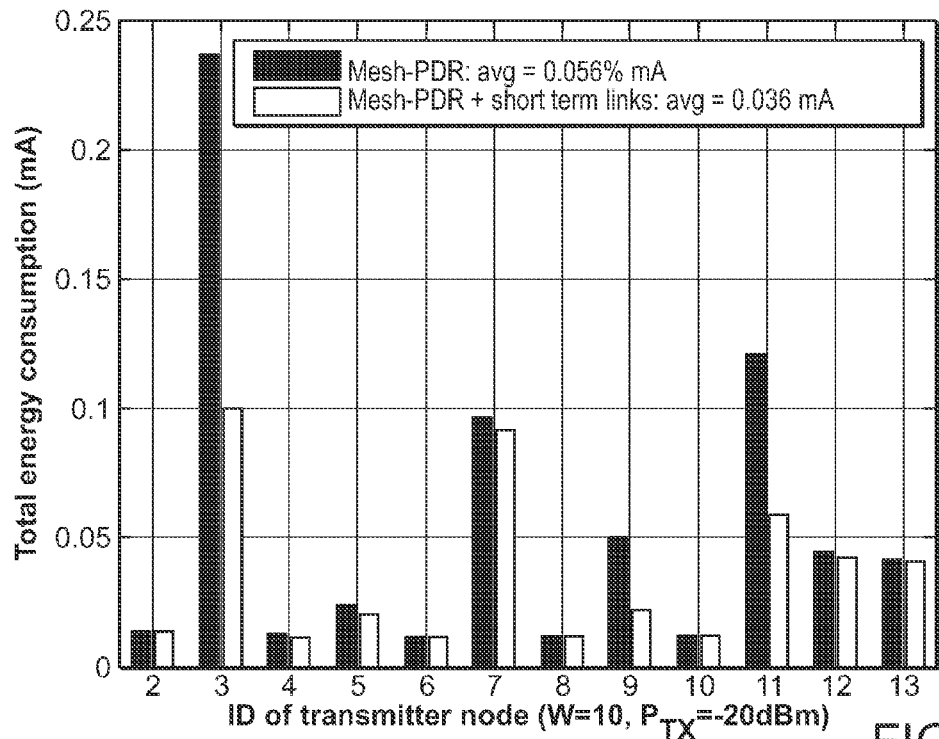
Figure 14:
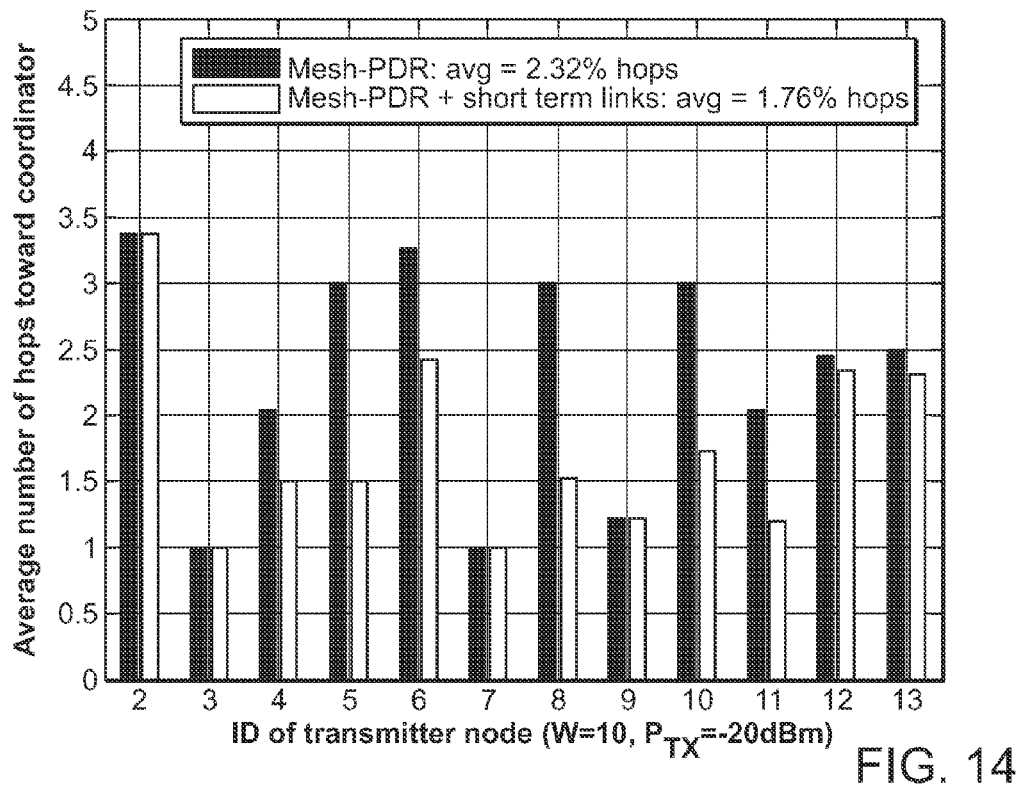

FIG. 3 shows three graphs as a function of time for three different radio links, FIG. 4 is a flowchart showing different steps of the method of the invention, FIG. 5 shows six graphs as a function of time showing on the one hand the attenuation of the power received and on the other hand the connectivity (i.e. the possible reception of packets) for three different radio links, FIG. 6 is a graph showing the interpretation of the connectivity of a radio link in terms of contact and intercontact times as a function of time using a deterministic approach, FIG. 7 is a graph showing the interpretation of the connectivity of a radio link in terms of contact and intercontact times as a function of time using a probabilistic approach, FIG. 8 is a block diagram of a device of the invention for implementing the FIG. 4 method, FIG. 9 is a diagram of a wireless body area network of the invention having some links active to illustrate the method of the invention, FIG. 10 shows three graphs concerning the evaluation of the quality of the links, FIG. 11 shows a graph of a body area network communication architecture, FIG. 12 shows a comparative graph of the packet delivery rate for various transmitter nodes of the body area network and different routing strategies, FIG. 13 shows a comparative graph of energy consumption for various transmitter nodes of the body area network, and FIG. 14 shows a comparative graph of the average number of hops to route a packet to the coordinator device of the network.

In all the figures, the same elements have the same reference numbers.

The following terminology is used hereinafter:

BAN: body area network, which may be constituted of a plurality of wireless devices, sensors (or nodes) situated on a mobile body, in particular a human body.

SNR: signal-to-noise ratio.

RSSI: received signal strength indicator; hardware type link quality indicator, relating to the power of the received signal.

LQI: link quality indicator; hardware type link quality indicator, relating to the level of the decision or estimation metrics used for demodulation, synchronization of the received signal.

NLOS: non-line-of-sight; situation of obstruction of radio links when the emitter and the receiver are not in direct view of each other.

LOS: line-of-sight; propagation of a wave when the transmitter and the receiver are in direct view of each other.

"Logical link": abstraction from a physical radio link reflecting the network connectivity between a pair of wireless devices (i.e. a possible link allowing transmission and reception of packets).

"Intermittently reliable link or link reliable in the short-term": a link the reliability/performance of which varies because of the mobility of the body and the repetitive movement of the members, but intermittently experiencing conditions favourable to communication (e.g. in terms of packet reception/loss).

"Link reliable in the long-term or quasi-permanently reliable link": a link whose reliability/performance is quasi-permanent over time, whatever the mobility or posture of the human body.

"Contact time": time during which a logical link is established between a pair of wireless devices or nodes of the body area network BAN and remains reliable according to a certain criterion or application success rate (e.g. in terms of packet reception/loss).

"Intercontact time": when a logical link is broken (following loss of one or more packets), the intercontact time corresponds to the necessary time before the link is re-established.

"Network topology or architecture": the logical organization of the nodes constructed at the level of the network layer for routing/relaying information from a subset of radio links considered to be the most reliable.

Figure 1:
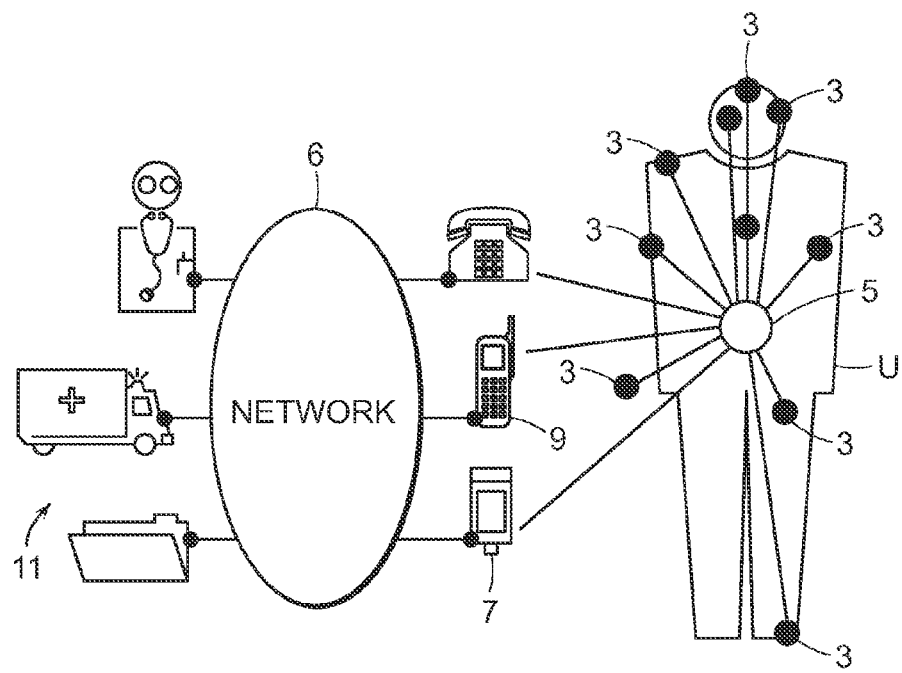
FIG. 1 is a diagram showing a wireless body area network.
Figure 2:
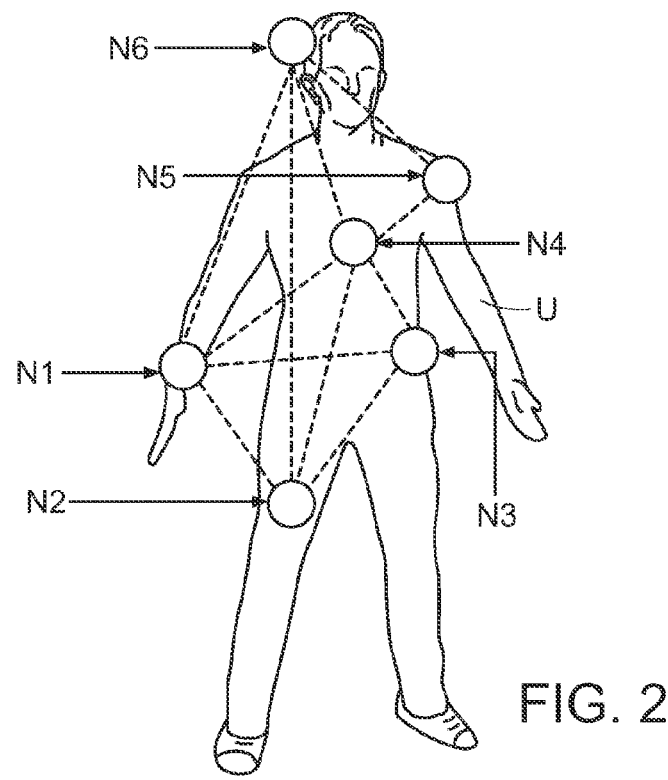
FIG. 2 is a diagram of a wireless body area network of the invention.

FIG. 2 is a diagram showing a user U equipped with six wireless devices each representing a node of the body area network, the nodes N1 on the right wrist, N2 on the right thigh, N3 on the left hip, N4 on the back at the rear, N5 on the left shoulder and N6 at the level of the right ear.

Each of these wireless devices N1 to N6 is for example equipped with a sensor for measuring a physical magnitude in relation to the body of the user U.

The nature of the sensor and the physical magnitude measured depend on the envisaged application of the body area network.

Envisaged are, for example, applications for navigation and/or positioning of groups of persons moving around inside buildings, as well as global positioning type services.

In another example, the sensors (e.g. accelerometers) measure magnitudes linked to movement, for example for tracking sports gestures or for entertainment and games applications.

In a further example, the application may comprise detection of posture or attitude, for example for rehabilitation, tracking vulnerable or aged persons, and surveillance of persons moving around in a hazardous environment (e.g. firefighters inside a burning building, etc.).

Also envisaged is a body area network for medical applications such as pacemakers, insulin pumps, surveillance/monitoring of vital signs (temperature, ECG, etc.). In this case the wireless devices include for example sensors measuring temperature, heart rate, blood pressure, etc.

In a further aspect applications are envisaged of "exploded terminal" type (screens, keyboards, earpieces not co-located).

Thus the present invention concerns any type of application using a wireless body area network in which wireless devices communicate with each other.

Accordingly, each of the nodes N1 to N6 may communicate with another node of the network provided that it is able to set up a radio link, indicated by dashed lines in FIG. 2.

As a function of diverse factors, for example too low a transmission power, a masking effect caused by the mobility of the user U and/or the distance between two nodes $N_i$-$N_j$ (i≠j), it may happen that a radio link cannot be established, or at least not established permanently.

The technologies used are short-range radio technologies, for example Zigbee™, Bluetooth™ Low Energy (BLE) or IR-UWB (Impulse Radio Ultra WideBand).

The transmission power associated with these wireless devices is generally considered low for health reasons (for example to minimize the impact of the emitted radio waves on health, etc.), to maximize the performance of other coexisting networks, for example telephony, WIFI, etc. networks (to minimize interference with other networks present in the vicinity of the body area network), and/or because of severe application constraints specific to body area networks (for example no maintenance/replacement of onboard batteries, network power continuity, small overall physical size of nodes, etc.).

FIG. 3 shows on three graphs the attenuation of the power received from the transmitted signal as a function of time for three respective different radio links from FIG. 2, namely N3-N5 for the top graph, N2-N6 for the middle graph and N1-N2 for the bottom graph.

The top graph in FIG. 3 shows an example of the attenuation of the power received from the transmitted signal between the nodes N3 and N5, i.e. the left hip and the left shoulder. Here the associated devices 3 and 5 are always in direct line-of-sight (LOS) with a low attenuation of the power received from the radio waves, here more than −40 dBm. This link is thus considered a link the performance of which (for example in terms of data packet delivery rate, attenuation level, signal to noise ratio, etc.) is stable and reliable in the long term.

On the other hand, in the middle graph, it is seen that the signal level between the nodes N2 (on the right thigh) and N6 (on the right ear) is strongly degraded (for example, the level of attenuation of the power received (here less than −60 dBm), the spread of the attenuation of the power received as a function of time, etc.), in quasi-permanent manner and/or unstable over time. Given their location, this is understandable, because the devices N2 and N6 are relatively far from each other. Similar behaviour will be obtained, for example, for the link between the nodes N3 and N4 which are not in direct line-of-sight (NLOS).

Then there are radio links, for example between N1 (at the level of the wrist) and N2 (at the level of the right thigh) the performance of which fluctuates because of the mobility of the body (or the quasi-repetitive or regular movement of the body and/or the limbs, etc.). The third graph shows for example the effect of the hand swinging relative to the body when walking. Thus the radio links alternate between phases in which performance is reliable (for example devices in direct line-of-sight (LOS), with a low level of attenuation of the radio waves and thus a high received power), and phases in which performance is degraded (for example in the case of link obstruction or NLOS with strong attenuation of the received signal). These are radio links reliable intermittently, oscillating between −45 dBm and −70 dBm, that it is proposed to evaluate and/or to qualify in order to be able to use them to transmit messages, although these links would not usually be employed in prior art body area networks.

FIG. 4 shows a flowchart of a method of transmitting messages in a wireless body area network comprising a plurality of wireless devices liable to communicate with each other.

In a step 10, messages are processed that have been received by at least one of the wireless devices $N_i$-$N_j$(i≠j, i,j being natural integer numbers) and the instantaneous quality of the corresponding radio links ($l_{i,j}$) is measured and times are estimated during and between which a radio link is reliable. A reliability indicator of the estimated times is calculated and the radio links are classified as a function of the reliability indicator into at least two categories ($T_{i,j}$) of which one relates to radio links that are intermittently reliable taking account of the mobility of the wireless devices of the body area network. This step 12 is shown in detail in the figure with substeps explained later.

Finally, during a step 14 for the transmission of messages across the body area network, the messages are routed via an "intermittently reliable" radio link during a period of time for which that same radio link is considered reliable, i.e. the classification results are taken into account for routing in the body area network. This enables optimization of the traffic of the body area network, for example in terms of energy consumption, message routing speed, latency, etc.

Where step 10 is concerned, the messages exchanged between the wireless devices N1 to N6 for example are service messages (i.e. messages useful for the organization and good management of the network), data messages or a combination of those messages.

Moreover, exchanging these messages periodically, pseudoperiodically or at a variable frequency is envisaged.

Exchanges are effected for example by sending specific "hello" type messages at predefined times for each of the wireless devices N1 to N6. Thus the receiver wireless device knows when it should receive a message and the source of that message (i.e. which wireless device is the sender). The absence of reception might be qualified as "radio link broken or non-existent".

Various scenarios are envisaged for exploiting these exchanges. In a first example, a direct communication between two wireless devices is used to estimate the quality of the radio link. In this case, it is a matter of a "Unicast" type point-to-point communication of which one of the devices is the addressee.

In another example, a "Broadcast" type direct communication is used to estimate the quality of the radio link vis-à-vis the transmitter. In this case, all the receiver wireless devices are addressees of this communication.

In a third example, a wireless device implementing the present invention listens to traffic or exchanges of data in clear on the communication channel in order to estimate the quality of the radio links between two other wireless devices. Exchanging an acknowledgement of reception reports good reception of the message.

In a fourth example traffic or exchanges of data in transit in clear on the body area network are listened to in order to estimate the quality of the radio links between pairs of wireless devices.

In a first embodiment, the instantaneous quality of the radio links is measured by measuring at least one radio metric such as RSSI, LQI or SNR.

In an alternative embodiment, the instantaneous quality of the radio links is measured by measuring a connectivity parameter, i.e. by determining only if the transmitted packet has been received and then demodulated (after detection of a synchronization correctly effected), independently of the quality of that demodulation.

To this end, the connectivity parameter and/or the radio indicator may be determined in binary fashion with a value "1" or a value "0" $L_{i,j}^{[t]}=\{0,1\}$ for any time t, between a node i and j, i≠j.

The radio indicator may be defined as follows:

$$L_{i,j}^{[t]} = \begin{cases} 1 & \text{if the radio indicator is greater than or equal to a threshold} \\ 0 & \text{if the radio indicator is less than a threshold} \end{cases}$$

The connectivity parameter is for example a packet reception rate, that is to say the number of packets received per unit time.

This connectivity parameter may be defined as follows:

At any time t, the state of the connectivity between a node Ni and Nj, i≠j, is $L_{i,j}^{[t]}=\{0,1\}$, where $$L_{i,j}^{[t]} = \begin{cases} 1 & \text{if the link is active, for example if a message has succeeded} \\ 0 & \text{if the link is inactive, for example if a message has failed} \end{cases}$$

Given the binary nature of the connectivity parameter and the radio indicator, both parameters may be used at the same time in the same body area network.

FIG. 5 respectively shows for the three links N3-N1, N6-N1 and N2-N1 from FIG. 2 a graph of signal level/attenuation of the power received as a function of time (left-hand graph) and a graph of the connectivity parameter (right-hand graph), defined on the basis of good reception (or not) of the packets.

This is therefore an example of instantaneous link quality measurements for a wireless device N1 vis-à-vis its three neighbour nodes N3, N6 and N2 (see FIG. 2).

This wireless device N1 for example uses periodic exchange of "hello" type control traffic to determine periodically and at each time the connectivity state vis-à-vis nodes present in its vicinity (i.e. the devices 3, 6 and 2 that are present within communication range).

The FIG. 5 graphs were obtained from experiments using 2.45 GHz wireless devices attached to a moving body (according to the FIG. 2 diagram) with periodic exchange of control traffic between the various nodes (a hello packet sent every 60 ms by each node). This was a channel survey with abstraction of a Bluetooth Low Emission type physical layer based on experimental SNR values.

As may be seen in FIG. 5, by knowing the frequency of sending the various "hello" packets, the device N1 is capable of periodically measuring the state of its connectivity vis-à-vis its vicinity.

The graph 30 of connectivity between the devices N3 and N1 shows quasi-permanent and reliable connectivity, interrupted only by a few losses of packets.

The graph 32 of connectivity between the devices N6 and N1 shows quasi-random connectivity, with high packet losses.

The graph 34 of connectivity between the devices N2 and N1 shows good connectivity over certain periods interrupted by periods of high packet loss.

Thus the connectivity associated with the various radio links varies with time and depends mainly on the state of the channel (left-hand graphs) in which the phenomena of propagation (for example attenuation of the signal, masking of the radio waves, etc.) and of mobility of the human body impact directly on the performance of the exchanges of data between the nodes in terms of good reception or loss of "hello" packets.

These measurements are then processed in the step 12 (see FIG. 4) to classify the various radio links after this first step 10 in order to characterize the performance of the various radio links on the basis of instantaneous and past connectivity information.

To be able to use the intermittently reliable radio links, it is necessary to classify them according at least to the two categories referred to above. Of course, a more refined classification with a plurality of levels of intermittently reliable radio links could be adopted.

To this end contact and intercontact times are determined during the step 12 from the respective connectivity parameter for two wireless radio link devices and the presence of repetitive patterns of intermittent contact is determined during a substep 12A.

The contact time $\hat{C}_{i,j}^{[t]}$ may for example be calculated as the duration of a binary sequence $L_{N+M}=\{L_{i,j}^{[1]}, L_{i,j}^{[2]}, \ldots, L_{i,j}^{[N+M]}\} \in \{1\}^N$ and $\{0\}^M$ and such that $$\frac{N-M}{N} \geq \gamma_F,$$

where $\gamma_F$ is a predetermined radio link reliability threshold. This amounts to determining the contact time as being the period of time for which the rate of reception of packets associated with this link is greater than or equal to the threshold $\gamma_F$, i.e. $PRR_{i,j}^{[t]}(\hat{C}_{i,j}^{[t]}) \geq \gamma_F$.

$\gamma_F$ is chosen as a function of the message transmission requirements of the applications.

This threshold depends mainly on the constraints and/or the requirements of the applications. Thus this threshold may be very high for critical applications (e.g. medical applications, etc.) or looser for games, navigation, etc. type applications.

For a medical or surveillance application, for example, the threshold $\gamma_F$ may be chosen greater than or equal to 95%. Thus priority is assigned to the successful transmission of messages.

On the other hand, for a wireless body area network intended for games or navigation, this threshold $\gamma_F$ may be lowered to 80%. In this type of application the loss of a packet is less critical.

The intercontact time is defined in a similar way to the contact time. The intercontact time $\hat{I}_{i,j}^{[t]}$ may similarly be calculated as the duration of a binary sequence $L_{N+M} = \{L_{i,j}^{[1]}, L_{i,j}^{[2]}, \ldots, L_{i,j}^{[N+M]}\} \in \{1\}^N$ and $\{0\}^M$ and such that $N \leq \gamma_{UP}$, where $\gamma_{UP}$ is the maximum number of "1" tolerated during the intercontact time.

FIGS. 6 and 7 show examples of the evolution of the connectivity $L_{i,j}^{[t]} = \{0,1\}$ as a function of time in which the contact and intercontact times are interpreted on the basis of connectivity information using a deterministic approach and a probabilistic approach, respectively.

As seen in FIGS. 6 and 7, the contact time of a radio link corresponds to the time for which a link is established and remains reliable (or connected). As soon as a link is broken (following loss of one or more packets), the intercontact time corresponds to the necessary time before the link is re-established.

Given the specific features inherent to wireless body area networks, notably linked to the quasi-periodic and repetitive mobility of the body or the limbs, these contact and intercontact times are deemed to vary more or less "regularly" or periodically over time as a function in particular of the speed of motion or of the posture of the wearer's body.

Accordingly, for a given radio link, if the evaluated contact and intercontact times evolve in a stable manner over time, it is highly probable that this link is of the type reliable in the short-term (provided that the time is judiciously chosen), that is to say intermittently reliable.

In the contrary situation, if the evaluated contact and intercontact times are very variable from one evaluation to another, then it is highly probable that this link is not reliable.

Other algorithms may be envisaged for estimating these contact and intercontact times on the basis of a history of connectivity measurements between a pair of nodes.

For example, shape (or pattern) recognition techniques and/or automatic learning techniques (e.g. hidden Markov models, neural networks, etc.) may be used to determine from raw connectivity information (the history H) the presence of a repetitive pattern of connection/disconnection of the link.

To proceed to the classification, it is therefore necessary to evaluate on the one hand these contact and intercontact times and on the other hand the stability of the evaluations over time, in order to detect among all the radio links a subset of links that are reliable in the short term or intermittently reliable (connectivity alternating periodically and repeatedly between states in which the link is reliable and other states in which the link is not reliable).

Given a temporal observation window of size W, at each time t, each wireless device $N^i$ has, on completion of the substep 12A, a history $H_{i,j}^{[t]}(W) = \{L_{i,j}^{[t-W+1]} \ldots L_{i,j}^{[t-1]} L_{i,j}^{[t]}\}$ representing the state of the connectivity (measured during the past time period W) vis-à-vis each device $N_j, \forall j \in \hat{n}^j \neq i$ present within communication range (see substep 12B).

Because there is a strong correlation between the performance of a radio link and the obstruction conditions, the contact time $\hat{C}_{i,j}^{[t]}$ (respectively the intercontact time $\hat{I}_{i,j}^{[t]}$) may ideally be calculated by counting the successive number of "1" (respectively "0") in the binary sequence $H_{i,j}^{[t]}(W)$ (FIG. 6 deterministic approach).

However, in the presence of local fading of the signal, packet losses are equally possible even if the link is not obstructed (LOS condition) and the transmission power is sufficient.

In order to take better account of the random aspect of the radio channel, a probabilistic approach is adopted, as shown in FIG. 7, enabling the loss of a predefined number of packets during a contact period to be tolerated.

To estimate the final contact and intercontact times (from estimated current and past times), an exponential smoothing technique is applied during a substep 12C:

$$C_{i,j}^{[t]}(\alpha_{CT}) = \alpha_{CT} \times C_{i,j}^{[t-1]} + (1-\alpha_{CT}) \times \hat{C}_{i,j}^{[t]}$$

$$I_{i,j}^{[t]}(\alpha_{CT}) = \alpha_{CT} \times I_{i,j}^{[t-1]} + (1-\alpha_{CT}) \times \hat{I}_{i,j}^{[t]}$$

where:
$\hat{C}_{i,j}^{[t]}$ (respectively $\hat{I}_{i,j}^{[t]}$) is the instantaneous (or current) estimate of the contact (respectively intercontact) time;
$C_{i,j}^{[t]}$ (respectively $I_{i,j}^{[t]}$) is the final estimate at time t of the contact (respectively intercontact) time; and, finally
$\alpha_{CT}$ is a forget factor for assigning more or less importance to past estimates.

To assess the stability of the various estimates, the moving coefficient of variation (MCV), $V_{i,j}^{[t]}$, is evaluated over a window of size $W_V$. The function of this coefficient is to assess the spread (or conversely stability) of the past $W_V$ evaluations of the contact and intercontact times. It is defined as being the ratio between the standard deviation and the mean of the estimates over a moving window of size $W_V$.

Accordingly, if this moving coefficient of variation $V_{i,j}^{[t]}$ is less than a certain threshold, $\gamma_V$, then the estimates are considered stable over time, thus indicating the presence of an intermittently reliable link, with regular and periodic contact and intercontact times. If not, if the moving coefficient of variation is greater than $\gamma_V$, then the estimates are considered too variable and the corresponding link is classified as not being reliable.

In accordance with envisaged variants, the stability may also be evaluated of a series of estimates (standard deviation, mean deviation, variance, sliding mean, coefficient of variation, etc.).

For evaluation of link quality in the long term or quasi-permanently, a WMEWMA (Window Mean with Exponentially Weighted Moving Average) estimator is used in the substep 12D, for example.

At each time t, and starting from the history $H_{i,j}^{[t]}(W)$ measured over a time period W vis-à-vis a neighbour node $N^j$, the WMEWMA estimator begins by evaluating the packet reception ratio (PRR):

$$PRR_{i,j}^{[t]}(W) = \frac{1}{W} \sum_{k=t-W+1}^{t} L_{i,j}^{[k]}$$

Finally, the WMEWMA estimator may be computed according to a moving exponential mean to estimate the quality of the radio link in the long term:

$$Q_{i,j}^{[t]}(W,\alpha_{LT}) = (1-\alpha_{LT}) \times Q_{i,j}^{[t-1]} + \alpha_{LT} \times PRR_{i,j}^{[t]}(W)$$

where:

$Q_{i,j}^{[t]}$ is the estimate or evaluation at time t of the quality of the link (i-j) between the wireless nodes or devices (Ni-Nj) in the long term;

$\alpha_{LT}$ is a forget factor enabling more or less importance to be assigned to past estimates; and, finally W is the size of the observation window.

Thus during the substep 12E the type ($T_{i,j}^{[t]}$) of each radio link may be accurately determined according to three main classes: links reliable over in long term or quasi-permanently thanks to the WMEWMA estimator, links reliable intermittently or in the short term thanks to the moving coefficient of variation $V_{i,j}^{[t]}$, and links that are not reliable.

From this information, a table of neighbours of the wireless device is updated during a substep 12F. This table is stored in a memory containing a list of the various neighbour wireless devices/nodes present within communication range with an evaluation of the type (reliable, intermittently reliable or not reliable) and properties of each radio link, for example.

These tables of neighbours stored in each wireless device may thereafter be used by:

1) an opportunistic routing algorithm to calculate an optimum path toward a destination as a function of certain application constraints (for example energy, delay);

2) an opportunistic and adaptive relaying algorithm for predicting the appearance of certain radio links to the destination nodes; or 3) a radiolocation algorithm for optimum scheduling of the measurement of the relative distances between the various nodes of the network as a function of the availability or unavailability of the radio links.

The invention also concerns a device 50 for transmitting messages across a wireless body area network comprising a plurality of wireless devices forming a body area network and liable to communicate with each other. FIG. 8 is a block diagram of such a device 50 of the invention for implementing the FIG. 4 method.

This transmission device 50 comprises on the one hand a device 52 configured to evaluate the quality of the radio links for a wireless body area network, that is to say to execute the steps 10 and 12, and on the other hand means 54 configured to route or to relay the messages via an intermittently reliable radio link during a period during which the intermittently reliable radio link is considered reliable. The means 54 are linked to the means 52 for evaluating the quality of the radio links and use the results produced by those means 52.

The device 52 for evaluating the quality of the radio links is configured to execute steps 10 and 12 of the method described above. It is for example a unit integrated into one or more wireless devices N1 to N6 of the body area network BAN with a processor and memories configured to execute the various steps of the above method and to store the results, for example in a table of neighbours. Of course, this unit may be specific to one sensor and/or wireless telecommunication unit or consist of the processor and memories of the wireless device already present.

Refer next to FIGS. 9 and 10.

FIG. 9 shows a user U with twelve wireless devices numbered N1 to N12 situated at various places on their body.

Of particular interest is the wireless device or node N1, which is the concentrator node to which all messages must be routed to communicate thereafter with an external network 6, for example (not shown in this figure).

FIG. 10 shows three graphs of which the top graph illustrates the long term quality estimator $Q_{i,j}^{[t]}$, the middle graph the contact and intercontact times defined above, and the bottom graph the moving coefficient of variation $V_{i,j}^{[t]}$.

Each graph is subdivided to show the evolution of these values as a function of time, respectively for the links between the nodes/wireless devices N1-N8, N1-N2, N1-N4 and N1-N3 (see also FIG. 9, concerning three different mobility speeds (1 m/s, 2 m/s and 3 m/s)).

Note that in this example each time interval (there are 12 intervals in total) corresponds to a simulation involving a radio link and a well defined mobility speed of the body. Each interval has a duration of 264 seconds, corresponding to an exchange of 4400 "hello" packets between the wireless devices at a frequency of one hello packet every 60 ms.

During the first three time intervals, the quality measurements corresponding to the radio link (N1-N8) are considered (this link being considered reliable in the short time), for three mobility speeds (1 m/s to 3 m/s).

In FIG. 10, a 90% threshold has been defined for deciding if a link is reliable in the long term. Note that with the WMEWMA estimator $Q_{i,j}^{[t]}$, the quality of the link is approximately 80% and the evaluation of the quality of the links in the short term is a good match to the mobility of the BAN and demonstrates contact and intercontact times with a very low coefficient of variation (<0.1). In this case the link is classified as being "intermittently reliable" or "reliable in the short term".

During the next three time intervals, the quality measurements corresponding to the radio link (N1-N2) are considered (the node N2 being situated behind the body relative to the node N1). Note that the long term quality of the link is on average equal to 50% and that the estimates of the contact and intercontact times are not stable, with a very high coefficient of variation. The link is therefore classified as "not reliable".

The measurements relating to the radio links (N1-N4) (intermittently reliable or reliable in the short term) and (N1-N3) (reliable in the long term) are considered next. It is again seen that the method of the invention adapts well to the various speeds and to the various types of link and enables determination of the performance of the various radio links both in the long term and the short term and classification thereof as a function of their characteristics with a view to their subsequent use by higher level protocols (e.g. routing, relaying, prediction, etc.).

Step 14 of the FIG. 4 method consists in using the various table of neighbours determined beforehand with a view on the one hand to probabilistic prediction based on the table of neighbours of the occurrence of intermittently reliable radio links and using those links for the transmission of messages, if any, with a view to improving the performance and the robustness of the higher level protocols, notably faced with the mobility of the body and the phenomena of propagation around and in the close proximity of the human body (e.g. masking and obstruction of radio links, multipath propagation, absorption of radio waves by the human body, etc.).

Thus each wireless device Ni, $\forall i \in n$ of the body area network has locally available a table of neighbours containing, for each of its neighbour nodes Nj (or nodes within communication range), $\forall j \in n^\wedge j \neq i$, an n-tuplet $\{Q_{i,j}^{[t]}, T_{i,j}^{[t]}, C_{i,j}^{[t]}, I_{i,j}^{[t]}, V_{i,j}^{[t]}, \}$:

where:

$Q_{i,j}^{[t]}$ is the quality of the link (Ni-Nj) in the long term, $T_{i,j}^{[t]}$ is the type of the link (Ni-Nj): reliable in the long term, reliable in the short term, not reliable, $C_{i,j}^{[t]}$ is the estimated contact time for the link (Ni-Nj), $I_{i,j}^{[t]}$ is the estimated intercontact time for the link (Ni-Nj),
$V_{i,j}^{[t]}$ is the moving coefficient of variation representing the spread (or stability) associated with the estimates $C_{i,j}^{[t]}$ and $I_{i,j}^{[t]}$.

This information is mainly used by the higher level protocols to:
- identify the presence of links reliable in the short term with a view to maximizing the performance of the routing and relaying protocols in terms of energy consumption, latency, data delivery rate, etc., and
- maximize the performance of the cooperative location algorithms by enabling optimum scheduling of the measurement of the distances between the nodes, thanks to the prediction of the appearance and/or disappearance of links reliable in the short term (from the information $T_{i,j}^{[t]}$, $C_{i,j}^{[t]}$, $I_{i,j}^{[t]}$ and $V_{i,j}^{[t]}$).

To transmit the messages, knowing the reliability of the radio links of the body area network, messages may now be routed via an intermittently reliable radio link during a time period for which the intermittently reliable radio link is considered reliable.

As a function of the application envisaged, transmission of a message via an intermittently reliable radio link is favoured to optimize at least one of the parameters from the following group: energy consumption, latency, data delivery rate.

Moreover, in some applications, measurements of the distances between the wireless devices may be scheduled taking account of the predicted appearance and/or disappearance of the intermittently reliable links.

An illustrative example is given hereinafter.
The various table of neighbours at the node/wireless device level may be used in different ways as a function of the application and a priority criterion/parameter assigned for the transmission of messages.

From information linked to the reception or non-reception of data packets, each node maintains in its table of neighbours a list of the wireless nodes in communication range and calculates a cost metric for each corresponding radio link. This cost metric depends mainly on the more important application constraints, for example the data delivery rate, the data routing delay or the energy consumption, and reflects the degree of reliability of each radio link or sequence of links (or path).

Given a body area network constituted of n wireless devices, the maximum number of (oriented) links is $n(n-1)$ and each existing logical link $l_{i,j}$ between a pair of nodes Ni and Nj, $i \neq j$, is assigned a cost metric denoted $e_{i,j}^{[t]}$.

Two main formulations of this cost metric may be envisaged, depending on the application constraints:
1) the probable delivery ratio (PDR) metric, for critical applications intolerant of packet losses; or
2) the average number of retransmissions (ANR) metric for applications highly constrained in terms of energy and delay.

The nonlimiting example given hereinafter considers the PDR metric. The ANR metric may be applied in a similar manner.

The PDR (Probability Delivery Ratio) metric is defined as the data delivery rate (or the quality of the link in the long term) and may be determined by a radio link quality estimator. Considering the WMEWMA estimator, the cost metric associated with each link $l_{i,j}$, $i \neq j$ is defined as follows: $e_{i,j}^{[t]} = Q_{i,j}^{[t]}$, where $Q_{i,j}^{[t]}$ is the estimated quality of the link $l_{i,j}$ in the long term (using WMEWMA).

In this case, at each time t and given a source node i and a destination node j, the optimal path $R_{i,j}$ connecting these two nodes is determined as being the path that maximizes the end-to-end reliability of communications in terms of data packet delivery, i.e.

$$R_{i,j} = \max_R \prod e_l^{[t]}.$$

The path $R_{i,j}$ calculated in this way and possibly consisting of a set of links of the network, is the path that maximizes the overall (or end-to-end) cost in terms of communication reliability.

This path may be calculated using a modified version of the Dijkstra shortest path calculation algorithm well known to the person skilled in the art.

FIG. 11 shows an application example that illustrates the impact of this routing metric on the performance obtained with opportunistic routing using intermittently reliable links.

FIG. 11 represents the connectivity graph associated with the FIG. 9 BAN in which the node N1 is considered the coordinator/concentrator node of the network and each link is assigned a cost metric relating to the data delivery rate (or the quality $Q_{i,j}^{[t]}$ of the link in the long term and reflecting the reliability of communication). It is assumed that the node N5 wishes to send a data packet to the coordinator N1.

In this graph, the solid line connections $l_{i,j}$ represent radio links reliable in the long term and the dashed line connections represent the intermittently reliable links. The numbers beside the lines express the cost of the radio link, namely $e_{i,j}^{[t]}$.

Considering the classic PDR routing metric using only links reliable in the long term, the optimum path is that which maximizes the data delivery probability.

Consequently, the optimum path selected is of length 3, $R_{5,1} = \{l_{5,11}, l_{11,3}, l_{3,1}\}$ with a total cost (or end-to-end reliability associated with the global path) equal to:

$$\prod_{l \in R_{5,1}} e_l^{[t]} = e_{5,11}^{[t]} \cdot e_{11,3}^{[t]} \cdot e_{3,1}^{[t]} = 1.$$

Accordingly, as may be seen, this metric tends to maximize the data delivery probability but at the cost of a significant increase in the length of the routing path and, in the end, the routing delay and the energy consumption.

If the radio links reliable in the long term and those reliable intermittently (i.e. in the short term) are considered, the routing process may still be optimized.

Thanks to the use of the method of the invention, the node 5 is able to determine the presence of a reliable temporary path in the direction of the coordinator 1 (for example the dashed line connection between the nodes N5 and N1 in FIG. 11).

The resulting opportunistic or adaptive routing algorithm functions as follows:

If at a given time this temporary link exists and is detected by the node N5, the data is sent directly to the coordinator N1.

If not, a path is calculated (using the PDR metric) and the data is relayed from node to node in the direction of the coordinator. Thus if possible transmission of messages is favoured via intermittently reliable links, if any, if their appearance can be predicted.

Opportunistic use is therefore made of the presence of certain radio links that are reliable and stable in the short term in order to minimize the length of the routing paths and in the end to minimize the energy consumption and the data routing delay.

Alternatively, if an intermittently reliable direct link is detected between a source node and a destination node, the choice may be made to send the data only when that link appears or is present.

When that link disappears temporarily, the source node may decide to delay its transmissions (even if an alternative and reliable path exists) until the intermittently reliable link reappears.

Simulations have been carried out to evaluate the contribution of the method of the invention compared to conventional routing architectures.

Multipoint-to-point (MP2P) traffic was considered in which each node/wireless device of the BAN (cf. FIG. 9 scenario) periodically sends a data packet in the direction of the coordinator (node N1). These data packets may for example contain distance measurements (e.g. radiolocation applications) or information relating to the human body (e.g. medical monitoring applications).

Two communication architectures are evaluated and compared hereinafter:

A multiple hop architecture using the PDR as the routing metric (referred to hereinafter as a "Mesh-PDR" architecture), in which each node determines the path that maximizes the end-to-end probability of data delivery to the coordinator. This is the standard scheme that uses only radio links that are reliable in the long term (links in solid line in FIG. 11).

An opportunistic or adaptive multiple hop architecture using the PDR as the routing metric (referred to hereinafter as a "Mesh-PDR+"short term" links" architecture) in which each node determines:

1) a temporary, reliable and direct path vis-à-vis the coordinator N1 taking account of the intermittently reliable radio links, or, where applicable 2) the path that maximizes the probability of delivery of the data to the coordinator N1.

It is moreover assumed that all these architectures rely on a communication mode without using retransmission mechanisms and calculation of paths using a Dijkstra algorithm.

Three performance metrics are of particular interest:

1) the overall energy consumption;

2) the data delivery rate calculated as the ratio between the number of packets received by the coordinator to the total number of packets transmitted; and, finally 3) the data routing delay.

The overall energy consumption is calculated proportionately to the number of packets received and transmitted by the wireless devices and the time periods for which these nodes are active.

The simulation results obtained are shown in FIGS. 12, 13 and 14, respectively (the speed of the BAN is 1 m/s, the "hello" packet sending period is 60 ms, and the transmission power is −20 dBm).

FIG. 12 shows the data delivery rate per node. It is seen first of all that for the "Mesh-PDR" architecture (standard multiple hop communication architecture) the data delivery rate (from the nodes N2-N13 to the coordinator N1) is on average equal to 94.89%.

Using the method of the invention, which takes account of intermittently reliable radio links and favours the transmission of messages via those radio links when they appear ("Mesh-PDR+short term" architecture) does not generate any significant loss of performance relative to the conventional routing architecture, with an average data delivery rate of 94.28%.

On the other hand, differences are seen when these architectures are analyzed from the energy consumption point of view.

FIG. 13 shows the energy consumption per node. Note first of all that this consumption is not uniform. In multiple hop architectures some nodes, as well as transmitting their own packets, are liable to relay packets of their neighbour nodes, thus increasing the overall energy consumption and the data routing delay.

In FIG. 13 for the conventional "Mesh-PDR" architecture, there is seen the presence of three significant energy consumption peaks corresponding to the nodes N3 and N11, which are main relay nodes for the nodes situated on the mobile limbs and low down on the body, and the node N7 (the main relay node for the nodes situated behind the body and at head level).

On the other hand, the new "Mesh-PDR+short term links" architecture enables an overall energy consumption saving of approximately 30% compared to the standard "Mesh-PDR" architecture whilst guaranteeing the same data delivery rate (see FIG. 12).

Finally, FIG. 14 shows the average number of hops per node toward the coordinator N1. This metric reflects the length of the routing paths and directly influences the data routing delay obtained.

It is seen that using the method of the invention enables an overall reduction of approximately 24% of the length of the routing paths compared to the "Mesh-PDR" architecture, thanks to astute use of the intermittently reliable links. This improvement may reach 50% in some cases (e.g. link N1-N8), thus significantly reducing the data routing delay.

It is therefore clear that the methods of the invention enable the performance of body area networks with wireless devices to be improved in terms of connectivity, energy consumption, latency, reliability, data delivery rate, reliability of communications, and robustness of protocols, in the face of the dynamic variation of the propagation conditions and/or the mobility of the human body, without generating high additional costs.

The invention claimed is:

1. A method for evaluating quality of radio links for a wireless body area network comprising at least first and second wireless devices positioned on parts of a body forming a body area network and configured to communicate with each other, at least one of the two wireless devices being mobile relative to the other, said method comprising exploiting messages received by at least one of the wireless devices to measure instantaneous quality of a corresponding radio link and to estimate times during and between which a radio link is reliable, calculating an estimated times reliability indicator, and classifying the radio links as a function of said reliability indicator into at least first and second categories, one of which is a category relating to intermittently reliable radio links taking into account the mobility of the wireless devices of the body area network, and routing or relaying messages via an intermittently reliable radio link during periods in which the intermittently reliable radio link is considered reliable and not during periods when the intermittently reliable radio link is considered not reliable; wherein a radio link is considered reliable when a logical link is established between said at least first and second wireless devices and a radio link is considered not reliable when a logical link is not established between said at least first and second wireless devices; and wherein the reliability of the intermittently reliable radio link varies due to the at least first and second wireless devices being mobile relative to each other caused by the mobility of the parts of the body on which the at least first and second wireless devices are positioned.

2. The method of claim 1, further comprising selecting the messages from the group consisting of service messages, data messages, and a combination of service messages and data messages.

3. The method of claim 1, wherein the messages are exchanged periodically.

4. The method of claim 1, wherein the messages are exchanged at a variable frequency.

5. The method of claim 1, further comprising evaluating the instantaneous quality of the radio links by measuring at least one radio indicator.

6. The method of claim 5, wherein, at a given time t, at least one of a connectivity parameter representative of an instantaneous quality of a radio link between two distinct nodes i and j and the radio indicator representative of an instantaneous quality of a radio link between two distinct nodes i and j is defined by a binary variable $L_{i,j}^{[t]} = \{0,1\}$.

7. The method of claim 6, wherein the binary variable is set to a first value if the link is active and a second value if the link is inactive.

8. The method of claim 7, wherein classifying the radio links as a function of said reliability indicator into at least first and second categories comprises determining, from at least one of the connectivity parameter and the radio indicator for two devices, contact and inter-contact times and the presence of repetitive patterns of intermittent contact.

9. The method of claim 8, further comprising calculating the contact time $\hat{C}_{i,j}^{[t]}$ at a time t between two distinct nodes i and j to be a duration of a binary sequence $L_{N+M} = \{L_{i,j}^{[1]}, L_{i,j}^{[2]}, \ldots, L_{i,j}^{[N+M]}\} \in \{1\}^N$ and $\{0\}^M$ such that $$\frac{N-M}{N} \geq \gamma_F,$$

where $\gamma_F$ is a reliability threshold of the radio link, wherein M And N are integers.

10. The method of claim 9, further comprising calculating the inter-contact time at a time t between two distinct nodes i and j, $\hat{I}_{i,j}^{[t]}$ as being the duration of a binary sequence $L_{N+M} = \{L_{i,j}^{[1]}, L_{i,j}^{[2]}, \ldots, L_{i,j}^{[N+M]}\} \in \{1\}^N$ and $\{0\}^M$ such that $N \leq \gamma_{UP}$, where $\gamma_{UP}$ is the maximum number of occurrences of an inactive link tolerated during the inter-contact period.

11. The method of claim 10, further comprising calculating final contact and inter-contact times from the formulas $C_{i,j}^{[t]}(\alpha_{CT}) = \alpha_{CT} \times C_{i,j}^{[t-1]} + (1-\alpha_{CT}) \times \hat{C}_{i,j}^{[t]}$ and $I_{i,j}^{[t]}(\alpha_{CT}) = \alpha_{CT} \times I_{i,j}^{[t-1]} + (1-\alpha_{CT}) \times \hat{I}_{i,j}^{[t]}$ where $\hat{C}_{i,j}^{[t]}$ is an instantaneous estimate of contact time, $\hat{I}_{i,j}^{[t]}$ is an instantaneous estimate of inter-contact time, $C_{i,j}^{[t]}$ is a final estimate of contact time, $I_{i,j}^{[t]}$, is a final estimate of inter-contact time, and $\alpha_{CT}$ is a forget factor.

12. The method of claim 11, further comprising calculating a moving coefficient of variation $V_{i,j}^{[t]}$ over a window of size $W_V$ that is defined as being a ratio between standard deviation and mean of estimates over a moving window of size $W_V$, comparing the moving coefficient to a threshold $\gamma_V$, and classifying a link as being one of intermittently reliable and reliable based on a result of said comparison.

13. The method of claim 6, wherein the binary variable is set to a first value if the radio indicator is less than a threshold and to a second value otherwise.

14. The method of claim 5, wherein the radio indicator is selected from the group consisting of RSSI, LQI or SNR.

15. The method of claim 1, further comprising evaluating the instantaneous quality of the radio links by measuring a connectivity parameter.

16. The method of claim 1, further comprising, for each wireless device, storing the reliability of the radio links associated with the device in a table of neighbors.

17. The method of claim 1, further comprising selecting an intermittently reliable radio link for transmission of a message to optimize at least one parameter selected from the group consisting of energy consumption, latency, and data delivery rate.

18. The method of claim 17, further comprising measuring distances between wireless devices based on a schedule that accounts for predicted appearance and disappearances of intermittently reliable links.

19. A system for evaluating quality of radio links for a wireless body area network, comprising at least first and second wireless devices positioned on parts of a body forming a body area network and configured to communicate with each other, at least one of the two wireless devices being mobile relative to the other, at least one of the wireless devices includes a first device configured to measure instantaneous quality of a corresponding radio link and to estimate times during and between which said radio link is reliable, said first device configured to calculate an estimated times reliability indicator and classify the radio links as a function of said reliability indicator into at least first and second categories, one of which is a category relating to intermittently reliable radio links taking into account the mobility of the wireless devices of the body area network; the at least one of the wireless device further includes a second device configured to route or relay messages via the intermittently reliable radio link during a period in which the intermittently reliable radio link is considered reliable and not during periods when the intermittently reliable radio link is considered not reliable; wherein a radio link is considered reliable when a logical link is established between said at least first and second wireless devices and a radio link is considered not reliable when a radio link is not established between said at least first and second wireless devices; and wherein the reliability of the intermittently reliable radio link varies due to the at least first and second wireless devices being mobile relative to each other caused by the mobility of the parts of the body on which the at least first and second wireless devices are positioned.

20. An apparatus for transmitting messages across a wireless body area network, said apparatus comprising a first device configured to evaluate a quality of radio links in the wireless body area network for communication between wireless devices, and a second device configured to route messages via an intermittently reliable radio link during a period during which the intermittently reliable radio link is considered reliable.

* * * * *